(12) United States Patent
Tweardy et al.

(10) Patent No.: US 6,254,560 B1
(45) Date of Patent: Jul. 3, 2001

(54) CERVICAL COLLARS

(75) Inventors: Lisa A. G. Tweardy, Thalwil (CH); Clay A. Burns, New York, NY (US); Karl T. Ulrich, Narberth, PA (US)

(73) Assignee: The Jerome Group, Inc., Moorestown, NJ (US)

( * ) Notice: Subject to any disclaimer, the term of this patent is extended or adjusted under 35 U.S.C. 154(b) by 0 days.

(21) Appl. No.: 09/093,559

(22) Filed: Jun. 8, 1998

(51) Int. Cl.⁷ ................................................. A61F 5/00
(52) U.S. Cl. ................................. 602/18; 128/DIG. 23
(58) Field of Search ................ 602/17, 18; 128/DIG. 23

(56) References Cited

U.S. PATENT DOCUMENTS

| | | |
|---|---|---|
| Re. 32,219 | 8/1986 | Garth . |
| 3,916,885 | 11/1975 | Gaylord, Jr. . |
| 4,205,667 | 6/1980 | Gaylord, Jr. . |
| 4,413,619 | 11/1983 | Garth . |
| 4,502,471 | 3/1985 | Owens . |
| 4,520,801 | 6/1985 | Lerman . |
| 4,538,597 | 9/1985 | Lerman . |
| 4,677,969 | 7/1987 | Calabrese . |
| 4,702,233 | 10/1987 | Omicioli . |
| 4,708,129 | 11/1987 | Pujals, Jr. . |
| 4,712,540 | 12/1987 | Tucker et al. . |
| 4,886,052 | 12/1989 | Calabrese . |
| 5,038,759 | 8/1991 | Morgenstern . |
| 5,180,361 * | 1/1993 | Moore .................................... 602/18 |
| 5,366,438 | 11/1994 | Martin, Sr. . |
| 5,437,612 * | 8/1995 | Moore .................................... 602/18 |
| 5,520,619 * | 5/1996 | Martin .................................... 602/18 |
| 5,622,529 * | 4/1997 | Calabrese ............................... 602/18 |
| 5,632,722 | 5/1997 | Tweardy et al. . |
| 5,797,713 | 8/1998 | Tweardy et al. . |

* cited by examiner

*Primary Examiner*—Michael A. Brown
(74) *Attorney, Agent, or Firm*—Schnader Harrison Segal & Lewis LLP (57) ABSTRACT

A cervical collar in which a sternum brace has an extension extending below the clavicle of the patient and to which a footplate is attached so that the footplate rests on the sternum of the patient. Also, certain components of the cervical collar, for example a jaw support and the sternum brace, are secured together to permit relative sliding movement between these components. Further, to accommodate the differences in the anatomy of a child from the anatomy of adult, the jaw support is mounted to the sternum brace so that the jaw support is disposed below the shoulder of a patient and an occipital support is mounted to a back support at an angle greater than forty-five degrees.

19 Claims, 10 Drawing Sheets

CERVICAL COLLARS

TECHNICAL FIELD

The present invention relates, in general, to orthopedic units and, in particular, to cervical collars which (a) redistribute the weight of the collar from the shoulders of the patient to the sternum of the patient, (b) have the facility for angular adjustment between the jaw support and the sternum brace which form a front portion of the cervical collar and the occipital support and the back support which form a back portion of the cervical collar, and (c) have improved effectiveness in providing head support for a patient.

BACKGROUND OF THE INVENTION

Various cervical collars have been developed for treating conditions of the neck and the cervical spine. Some of these collars which are arranged to handle whiplash and other such injuries, where support for the head and neck of the patient is needed, function to partially immobilize the head and neck of the patient and relieve spasm or strain to which the neck muscles of the patient might be subjected by transferring weight or force from the head of the patient to the shoulders or adjacent areas of the patient. Other collars, arranged for complete or near complete immobilization of the head and neck of the patient, also have been developed.

Unfortunately, many patients using cervical collars develop decubitus or decubitus ulcers (also known as bed sores, pressure sores, or trophic ulcers) when wearing cervical collars. These ailments, which involve a breakdown of tissue overlying a bone, arise when tissues overlying a bony prominence are subjected to prolonged pressure against an object such as a cervical collar. In addition to affecting superficial tissues such as the skin, decubitus and decubitus ulcers also can affect muscle and bone.

Moisture and pressure are two of the major factors which contribute to the formation of decubitus. Once a decubitus ulcer forms, it is like an iceberg having a small visible surface with an extensive base of unknown size. There is no good method of determining the extent of tissue damage. Once started, decubitus can continue to progress through the skin and fat tissue to muscle and eventually to bone. Once started, decubitus is very difficult to treat and arrest. In extreme cases, surgical replacement of bone, muscle and skin are required to restore that portion of the body of the patient where decubitus has formed.

Consequently, it is desirable to eliminate or at least minimize the effect of pressure points when using cervical collars. The likelihood of contracting decubitus can be greatly reduced by a more even distribution of pressure to a number of parts of the body of the patient.

A feature, preferably included in cervical collars to overcome limited adaptability to accommodate the body of the patient and the particular ailment prompting the need for wearing a cervical collar, is the facility for adjusting the relative positions of various components of the cervical collar. Currently available cervical collars generally lack such a feature.

A shortcoming of currently available cervical collars worn by children is that they have been designed by simply scaling down adult cervical collars. Such designs fail to take into consideration the considerable difference in the anatomy of a child and the anatomy of an adult.

SUMMARY OF THE INVENTION

Accordingly, a cervical collar, constructed in accordance with the present invention, includes a sternum brace having an extension adapted to extend to below the clavicle of a patient and a padded movable footplate attached to the extension and adapted to rest against the body of the patient. This cervical collar also includes a back portion and means for attaching the sternum brace and the back portion together.

According to another aspect of the present invention, certain components of the cervical collar are attached by means which permit relative sliding movement to adjust the relative positions of the components. For example, a front portion of the cervical collar has a jaw support mounted to the sternum brace by means which permit relative sliding movement between the jaw support and the sternum brace and the back portion of the cervical collar has an occipital support mounted to a back support by means which permit relative sliding movement between the occipital support and the back support.

Yet another aspect of the present invention is the arranging the relative positions of a jaw support and a sternum brace and the relative positions of an occipital support and a back support to accommodate the anatomy of a child.

DETAILED DESCRIPTION OF THE INVENTION

Referring to FIGS. 1 and 3 through 5, a cervical collar, constructed in accordance with the present invention, includes a sternum brace 20 having an extension 22 adapted to extend to below the clavicle of a patient and a padded movable footplate 24 attached to extension 22 and adapted to rest against the body of the patient, namely against the sternum. Sternum brace 22 is symmetrical about a vertical center line.

Preferably, sternum brace 20 has a continuous padding 26 along the entire lower portion of the sternum brace, including footplate 24, where the sternum brace contacts the sternum and upper trapezius of the patient. Otherwise, the sternum brace 20, being made of a semi-rigid plastic material, could cause discomfort to the patient and might cause decubitus as unpadded portions of the sternum brace would rest against the body of the patient for long periods of time. Those parts of sternum brace 20 which do not contact the body of the patient may be left unpadded. Padding 26 can be attached to sternum brace 22 by releasable or non-releasable means such as hook and loop fasteners, adhesives, rivets or other suitable conventional arrangements.

Extension 22 includes a flexible hinge portion 22a by which padded movable footplate 24 is permitted to pivot and move toward and away from the sternum of the patient of the cervical collar. Hinge portion 22a should be sufficiently flexible to allow footplate 24 to rest comfortably on the sternum of the patient and inhibit decubitus but not so flexible that the necessary support or distribution of force and weight to the sternum is not provided.

For the embodiment of the invention illustrated in FIGS. 1 and 3 through 5, movable footplate 24 is releasable from extension 22 and padding 26. Footplate 24 can be attached to extension 22 by a hook and loop fastener, an adhesive, a rivet or other suitable conventional means.

Cervical collars, such as the those constructed in accordance with the present invention, often are used for trauma patients who have injuries other than those for which the cervical collar is used. Some patients may require, for example, a tracheotomy which might prevent use of a cervical collar which covers the throat. Accordingly, sternum brace 20 preferably has an opening 28 which allows for access to the throat of the patient.

Figure 1:
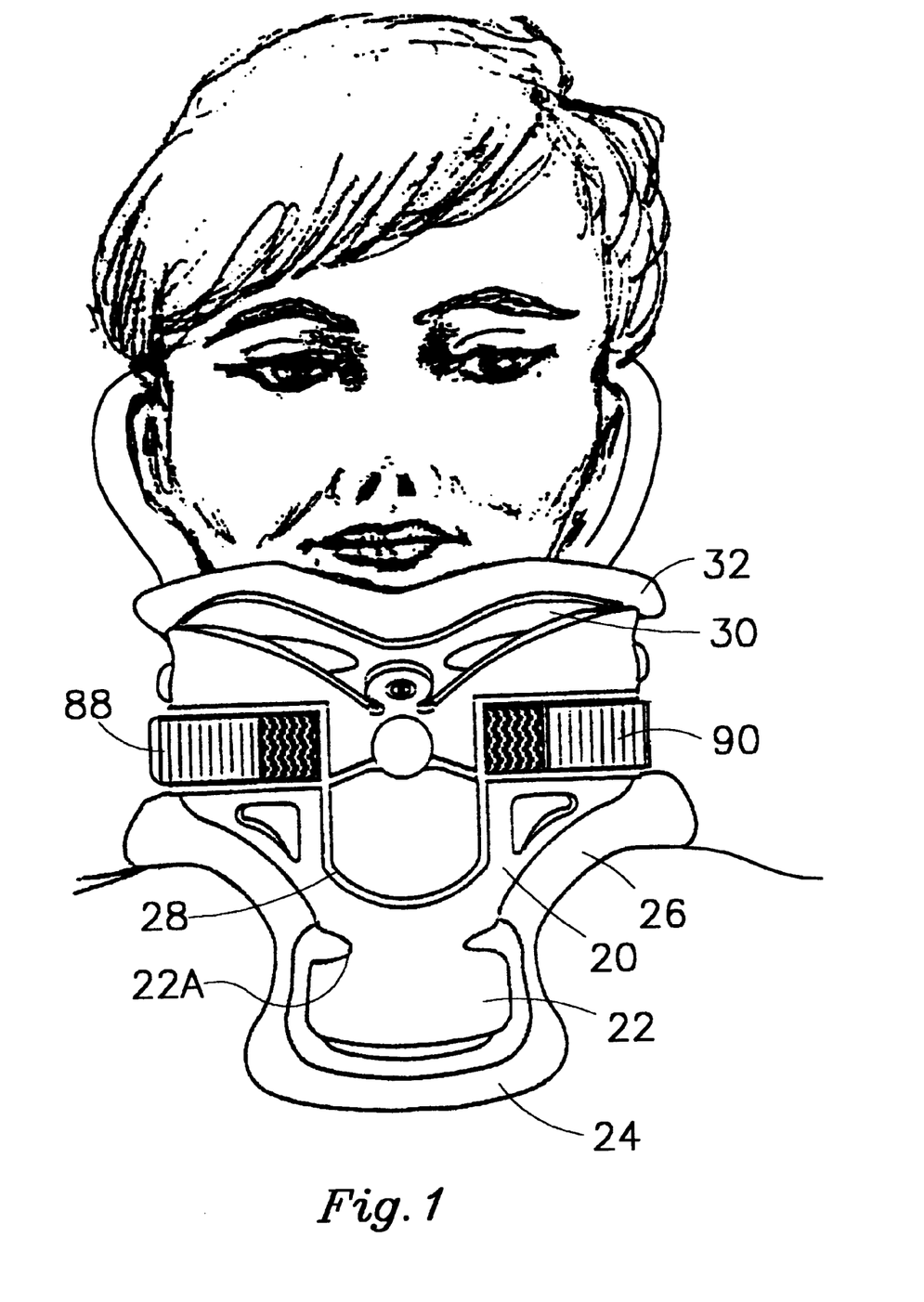
FIG. 1 is a front view of a first embodiment of a cervical collar, constructed in accordance with the present invention, as worn by a patient.
Figure 3:
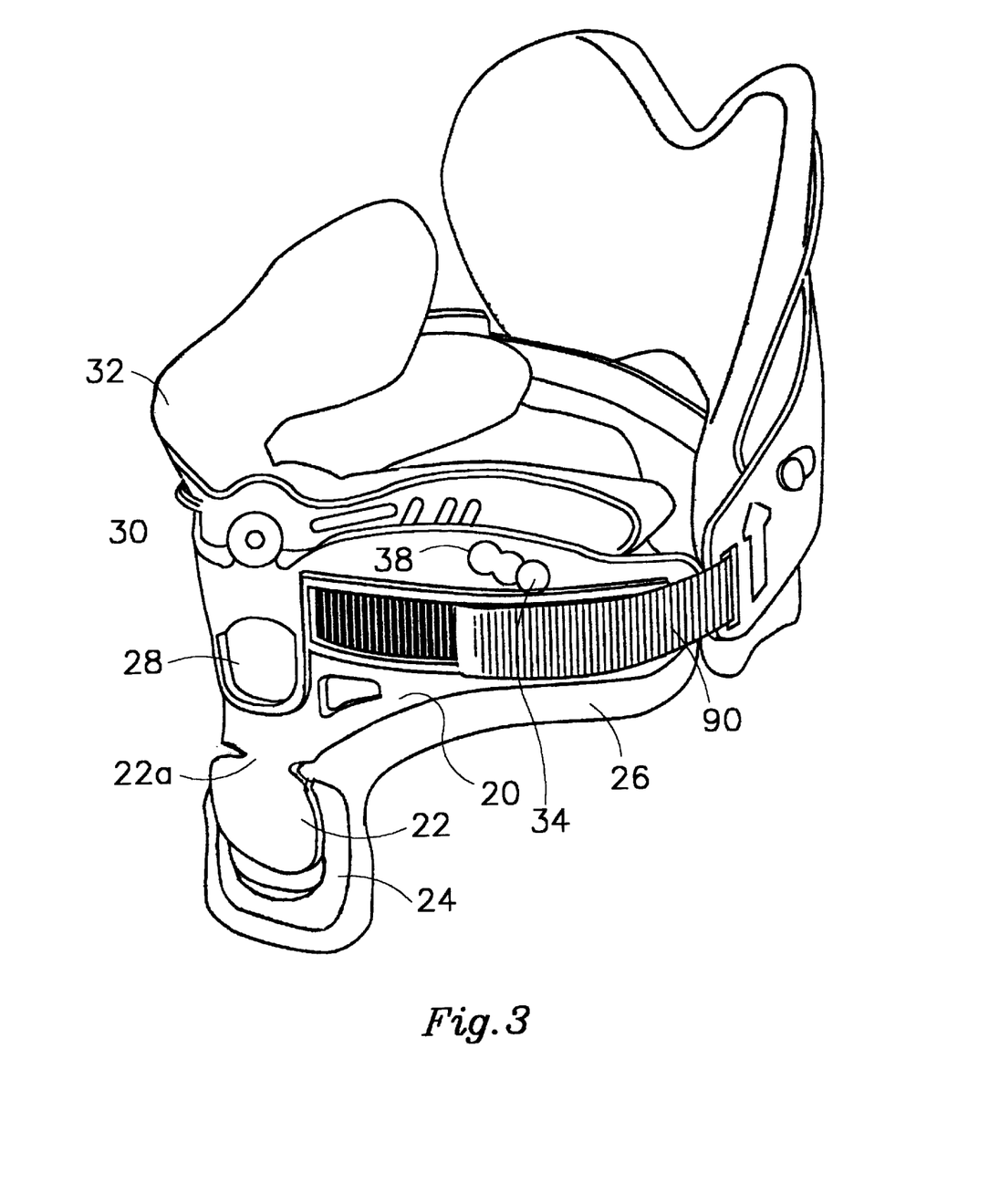
FIG. 3 is a front perspective view of the FIG. 1 cervical collar.
Figure 5:
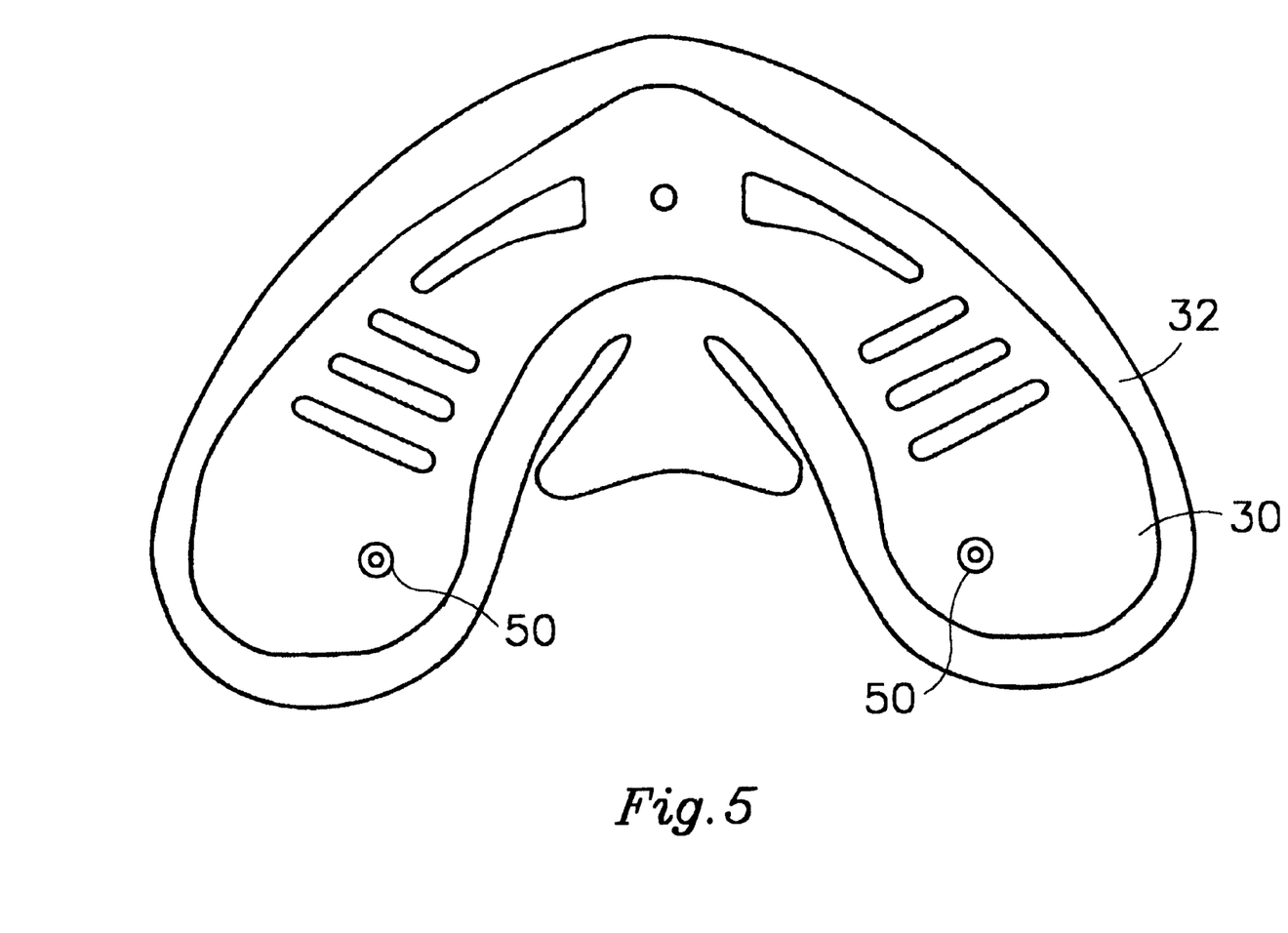
FIG. 5 is a front view of the jaw support of the FIG. 1 cervical collar.

A cervical collar, constructed in accordance with the present invention, also includes a jaw support 30 mounted to sternum brace 20 for relative sliding movement between the jaw support and the sternum brace. Preferably, jaw support 30 has a continuous padding 32 along the entire lower portion of the jaw support. Otherwise, the jaw support 30, being made of a semi-rigid plastic material, could cause discomfort to the patient and might cause decubitus as the jaw and the side of the head of the patient would rest against unpadded portions of the jaw support for long periods of time.

Jaw support 30 is mounted to sternum brace 20 for relative sliding movement between the jaw support and the sternum brace by first and second spaced apart fastener units 34 and 36 symmetrically disposed about the vertical center line of the cervical collar. Referring in addition to FIGS. 8A through 8D, each of fastener unit 34 and 36 includes a first female member 38 in sternum brace 20 and having first and second through-holes 40 and 42 extending along first and second parallel axes 44 and 46, respectively, and a through-passage 48 extending between first and second through-holes 40 and 42. Each fastener unit 34 and 36 also includes a second female member 50 in jaw support 30 and having a through-hole 52 extending along an axis 54 parallel to first and second axes 44 and 46 of first and second through-holes 40 and 42 in first female member 38.

Each fastener unit 34 and 36 further includes a male member 56 movable axially through first and second through-holes 40 and 42 in first female member 38 and through-hole 52 in second female member 50 and sidewise through through-passage 48 in first female member 38. Male member 56 has an enlarged head 58, a first shank portion 60 adjacent enlarged head 58, an enlarged tip 62, a second shank portion 64, and a third shank portion 66.

First shank portion 60 of male member 56 limits axial movement of the male member in a first direction (downward in FIGS. 8A, 8B and 8D) when the first shank portion abuts against a shoulder 67 in first female member 38. As shown most clearly in FIG. 8C, first shank portion 60 of male member 56 is sized relative to through-passage 48 in first female member 38 to prevent sidewise movement of the male member between first and second through-holes 40 and 42 in first female member 38 when the male member is in a first axial position.

Enlarged tip 62 of male member 48 inhibits axial movement of the male member in a second direction, opposite to the first direction (upward in FIGS. 8A, 8B and 8D), when enlarged tip 62 abuts against a shoulder 68 in second female member 50. Shoulder 68 in second female member 50 is formed to be sufficiently flexible to permit enlarged tip 62 and third shank portion 66 of male member 56 to be forced through through-hole 52 in second female member 50 for movement of the male member in the first direction, yet sufficiently resistant to unintended passage of third shank portion 66 and enlarged tip 62 through through-hole 52 for upward movement of the male member.

Figure 8A:
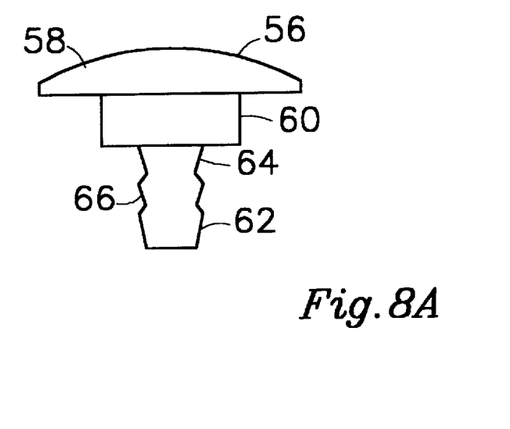
FIGS. 8A through 8D illustrate the components of a fastener unit which can be used to attach various parts of a cervical collar constructed in accordance with the present invention.
Figure 8B:
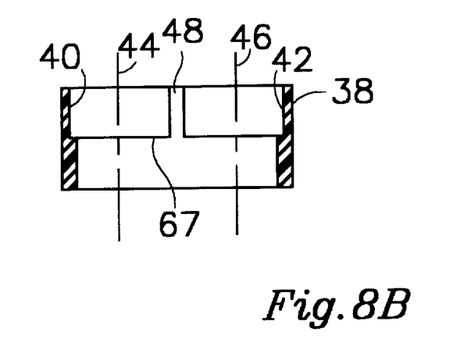
Figure 8C:
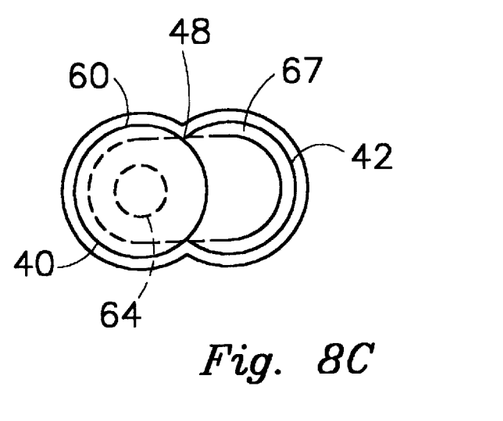
Figure 8D:
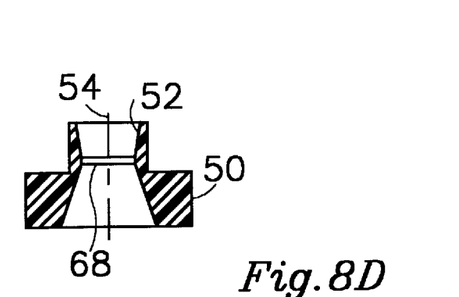

Second shank portion 64 of male member 48 is adjacent first shank portion 60 and, as shown most clearly in FIG. 8C, is sized relative to through-passage 48 in first female member 38 to permit sidewise movement of the male member between first and second through-holes 40 and 42 in first female member 38 when the male member is in a second axial position.

Third shank portion 66 of male member 48 is adjacent enlarged tip 62 is in bearing contact with shoulder 68 of second female member 50 and inhibits axial movement of the male member in the second direction when the male member is in the first axial position and free of bearing contact with shoulder 68 of second female member 50 when the male member is in the second axial position. As indicated above, shoulder 68 in second female member 50 is formed to be sufficiently flexible to permit enlarged tip 62 and third shank portion 66 of male member 56 to be forced through through-hole 52 in second female member 50 for movement of the male member in the first direction, yet sufficiently inhibit unintended passage of third shank portion 66 and enlarged tip 62 through through-hole 52 for upward movement of the male member.

In operation, male member 56 is passed through one of the through-holes 40 or 42 in first female member 38 in sternum brace 20 in the first (downward) direction until enlarged tip 62 and third shank portion 66 pass through through-hole 52 in second female member 50 in jaw support 30 beyond shoulder 68 in the second female member and first shank portion 60 of the male member abuts against shoulder 67 of the first female member. In this axial position of male member 56, first shank portion 60 of male member 56 is laterally aligned with through passage 48 and the male member is prevented from moving sidewise to the other through-hole in the first female member. This results in jaw support 30 being mounted to sternum brace 20.

When the relative positions of sternum brace 20 and jaw support 30 are to be changed, enlarged head 58 of male member 56 is gripped and pulled in the second (upward) direction until third shank portion 66 clears shoulder 68 in second female member 50 and second shank portion 64 is laterally aligned with through-passage 48 in first female member 38. In this axial position of male member 56, the male member can pass through through-passage 48 to the other through-hole in first female member 38 thereby adjusting the relative positions of sternum brace 20 and jaw support 30.

Figure 4:
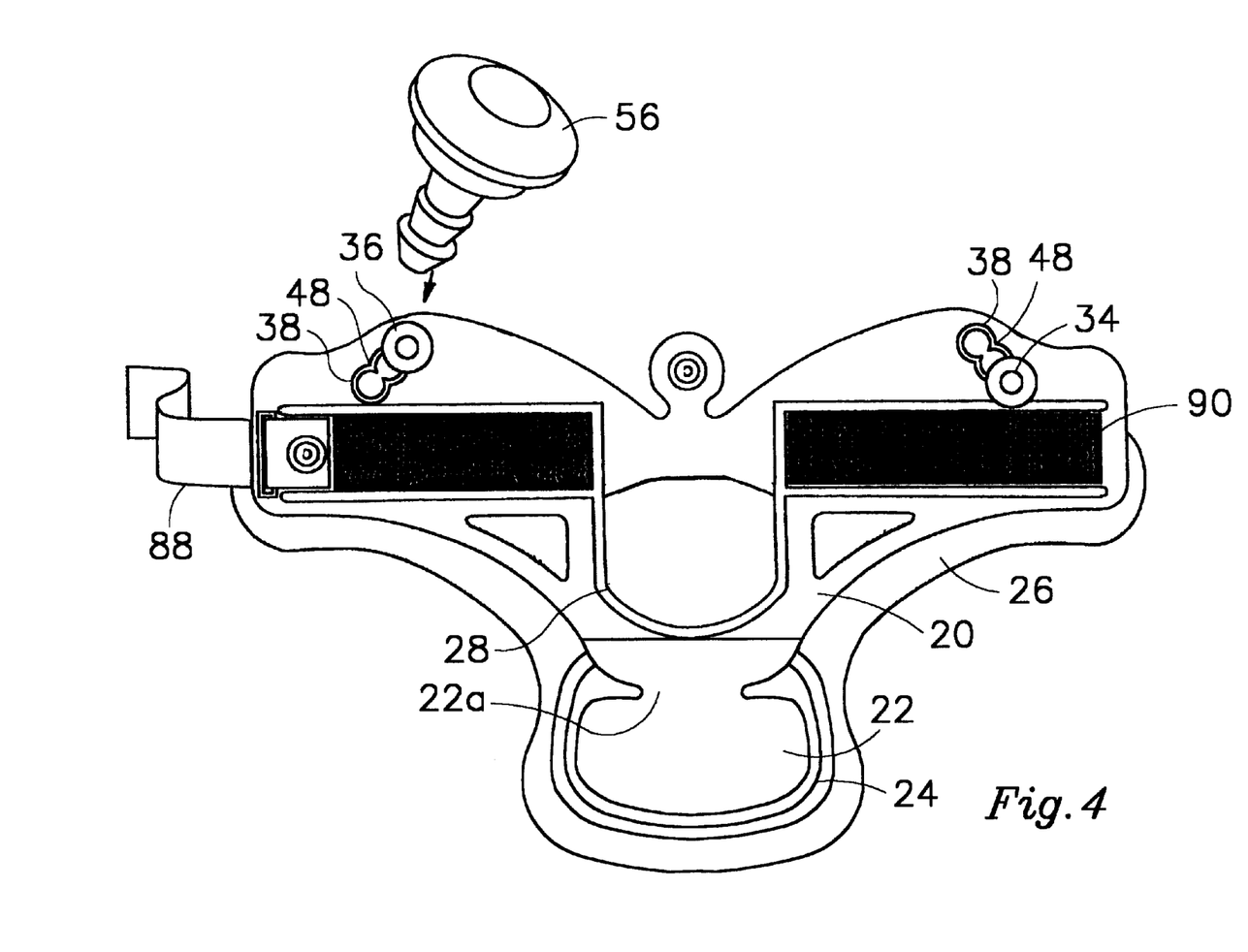
FIG. 4 is a front view of the sternum brace of the FIG. 1 cervical collar.

FIGS. 8A through 8D show a fastener unit having two through-holes and one through-passage in the first female member. As indicated by FIGS. 3 and 4, first female member 38 can be arranged with more through-holes and through-passages.

Figure 2:
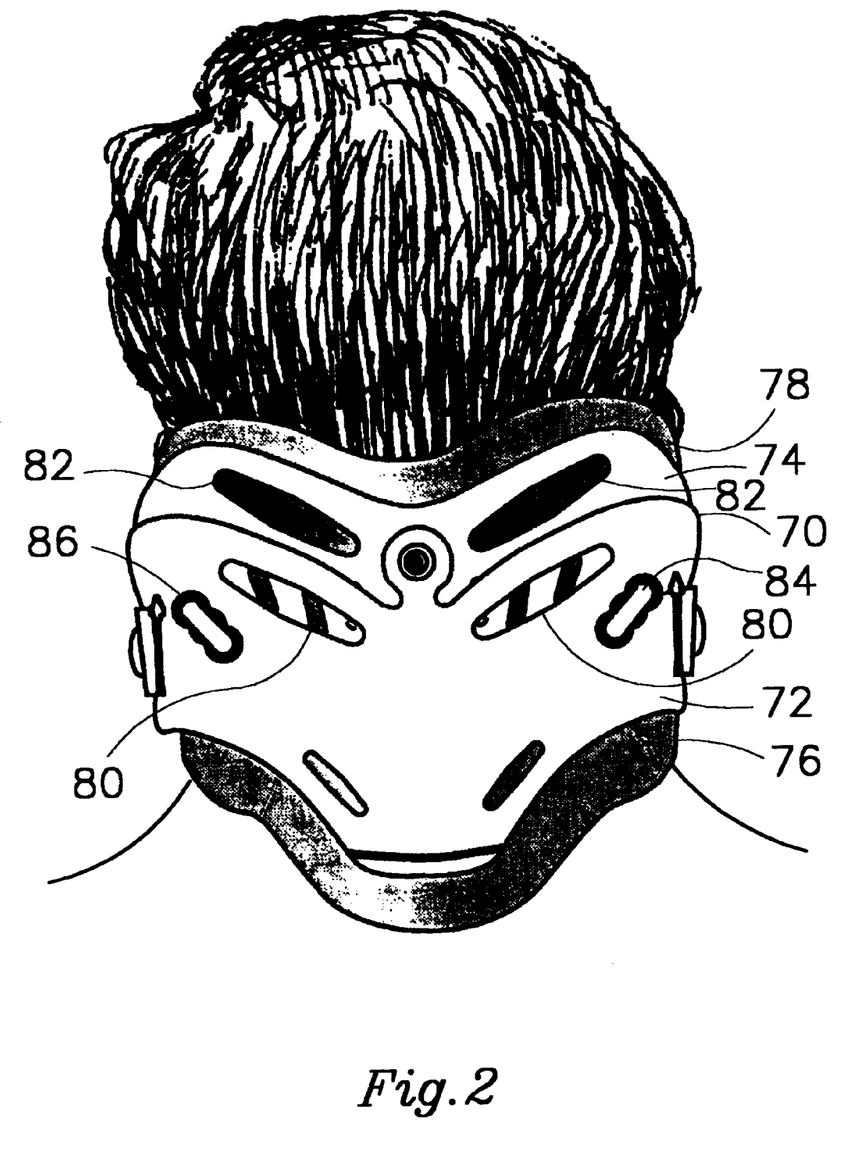
FIG. 2 is a rear view of the FIG. 1 cervical collar as worn by a patient.
Figure 6:
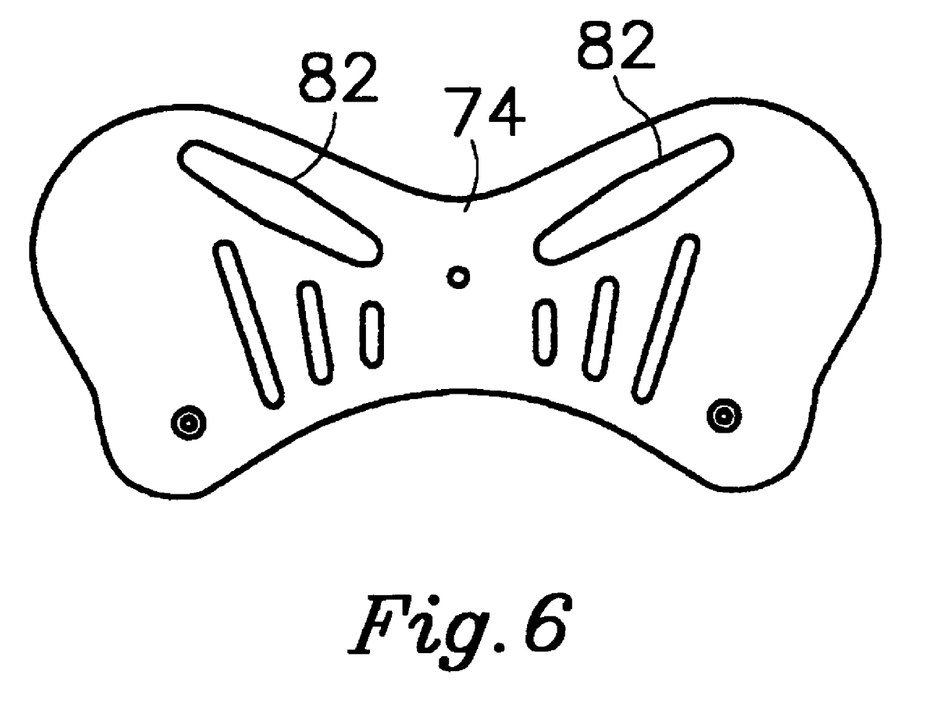
FIG. 6 is a front view of the occipital support of the FIG. 1 cervical collar.
Figure 7:
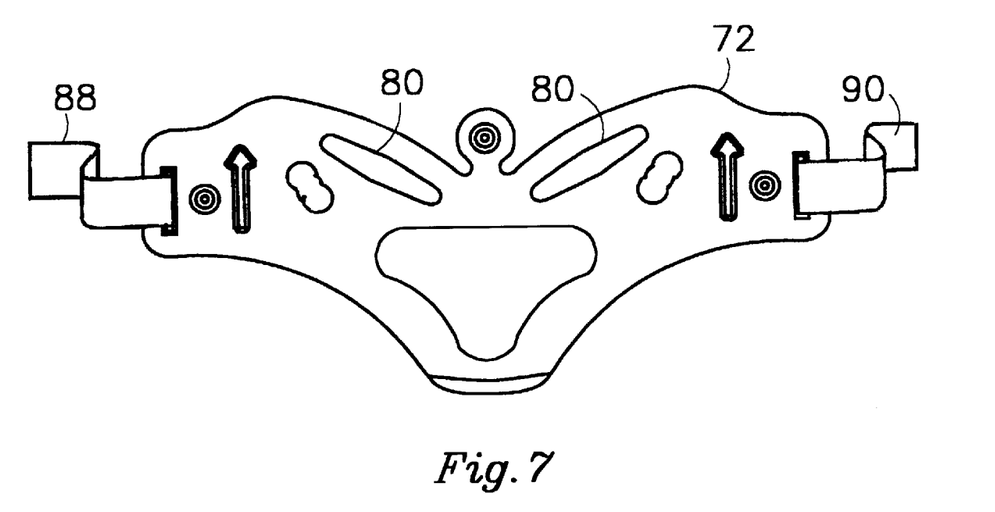
FIG. 7 is a front view of the back support of the FIG. 1 cervical collar.

Referring to FIGS. 2, 6 and 7, a cervical collar, constructed in accordance with the present invention, further includes a back portion 70 which has, for the embodiment of the invention being described, a back support 72 and an occipital support 74. Back support 72 has a continuous padding 76 and occipital support 74 has a continuous padding 78 where the back support and the occipital support are intended to rest against the back and head, respectively, of the patient. Padding 76 can be attached to back support 74 and padding 78 can be attached to occipital support 74 by adhesives, rivets or other suitable conventional means.

Back support 72 preferably is formed with recesses 80 to avoid placing pressure on the soft tissue of the back portion of the trapezius muscle and to distribute pressure to the upper back along the spine resulting in greater immobilization and patient comfort. Occipital support 74 preferably is formed with vents 82 which allow for passage of vapor from padding 78 through the occipital support.

Back support 72 and occipital support 74 are attached for relative sliding movement between the back support and the occipital support whereby the relative positions of the back support and the occipital support can be adjusted to allow for different head sizes and proper and even pressure distribution across the body of the patient. Fastener units 84 and 86, similar in construction and operation to fastener units 32 and 34 by which jaw support 30 is mounted to sternum brace 20, can be used to attach back support 72 and occipital support 74 together.

A cervical collar, constructed in accordance with the present invention, further includes means for attaching the front portion, composed of sternum brace 20 and jaw support 30, and back portion 40, composed of back support 72 and occipital support 74, together. As shown in FIGS. 1, 3, 4 and 7, such attachment means can include hook and loop fasteners 88 and 90.

Figure 9A:
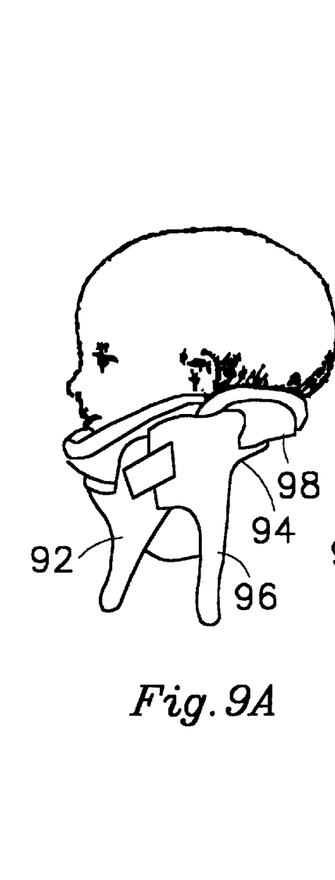
FIGS. 9A through 9C are side views of tree versions of another embodiment of a cervical collar constructed in accordance with the present invention as worn by a patient.
Figure 9B:
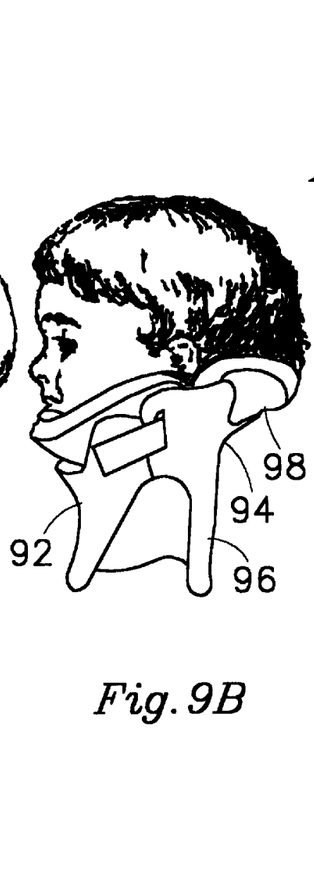
Figure 9C:
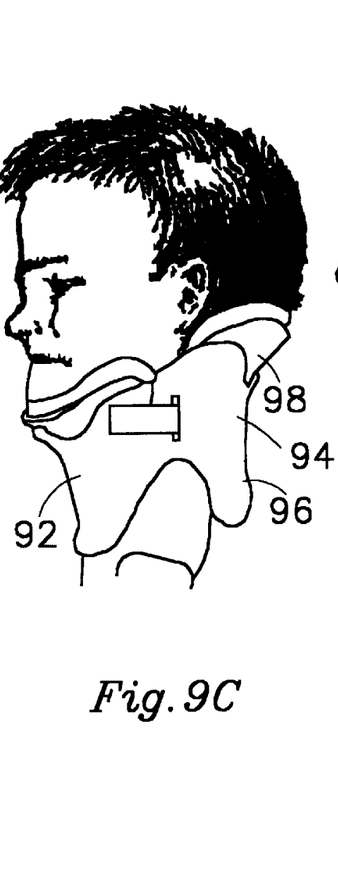
Figure 9D:
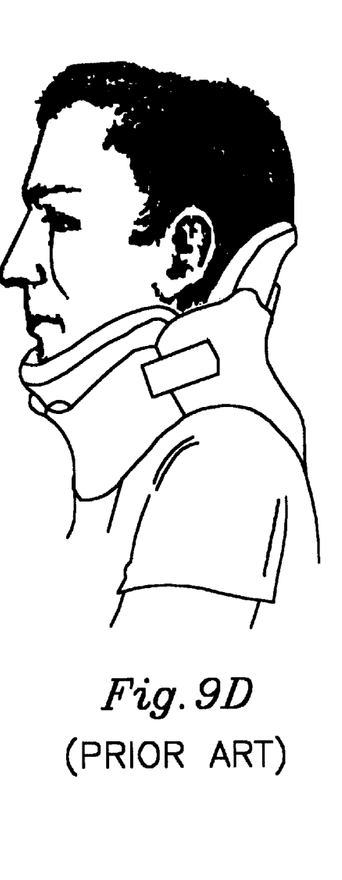
FIG. 9D is a side view of a prior art cervical collar as worn by a patient.

Another embodiment of a cervical collar, constructed in accordance with the present invention, is illustrated in FIGS. 9A, 9B and 9C. These Figures, when compared to FIG. 9D which illustrates a prior art cervical collar, shows the difference in the anatomy of a child and the anatomy of adult, particularly the back of the head relative to the back. Using the cervical collar shown in FIG. 9D on the infant shown in FIG. 9A will result in the tendency of the head to slip against the generally vertically disposed occipital support 90, thereby defeating the purpose of the cervical collar to provide support for the head of the infant.

Accordingly, as shown by FIGS. 9A, 9B and 9C, a cervical collar, constructed in accordance with the present invention, includes a front portion 92 and a back portion 94 having a back support 96 and an occipital support 98 with occipital collar mounted to back support 96 at an angle greater than forty-five degrees to the back support. With the progression of age, the back of the head projects less and less beyond the back, so that occipital support 98 is mounted to back support 96 at substantially ninety degrees for the infant cervical collar and approximately forty-five degrees for the youth cervical collar. Preferably, occipital support 98 is mounted to back support 96 for relative sliding movement between the occipital support and the back support by means such as fastener units 34 and 36.

Figure 10A:
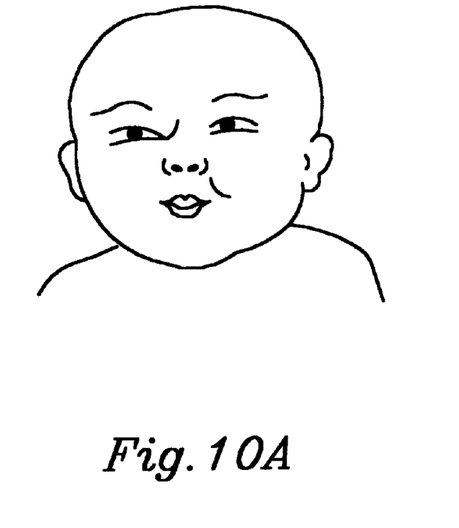
FIGS. 10A and 10B illustrate one difference between the anatomy of a child and the anatomy of an adult.
Figure 10B:
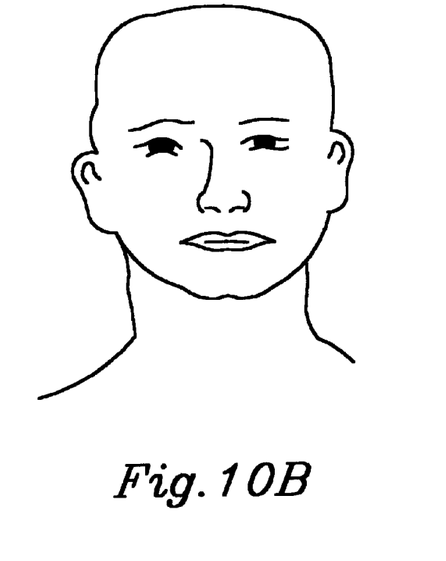

FIGS. 10A and 10B illustrate another difference in the anatomy of an infant and the anatomy of an adult. As shown in FIG. 10A, the chin of an infant is below the shoulder of the infant, while, as shown in FIG. 10B, the chin of an adult is above the shoulders of the adult. According to another aspect of the present invention, the cervical collars already described, when arranged for use with an infant, preferably include a jaw support mounted to a sternum brace so that the jaw support is disposed below the shoulders of a patient. Preferably, the jaw support is mounted to the sternum brace for relative sliding movement between the jaw support and the sternum brace by means such as fastener units 34 and 36.

Figures 11A, 11B:
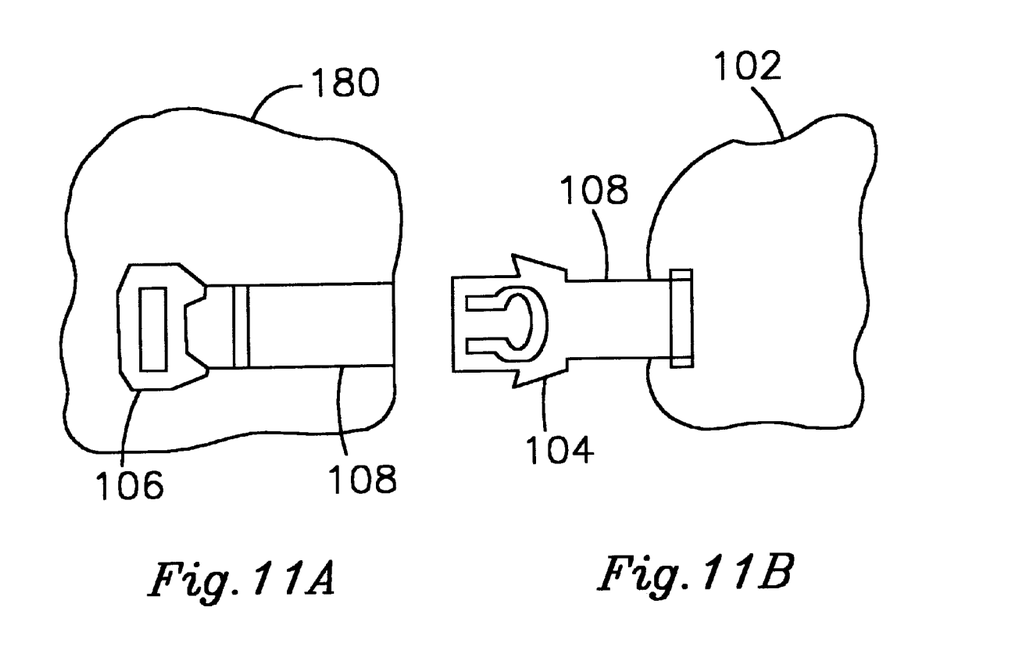
FIGS. 11A and 11B are front views of another embodiment of a cervical collar constructed in accordance with the present invention.

Another feature, preferably incorporated in a cervical collar constructed in accordance with the present invention, is illustrated in FIGS. 11A and 11B. To protect against inadvertent detachment of front portion 100 and back portion 102 of the cervical collar or undesired detachment of the front portion and the back portion by a child, a snap buckle of suitable design and operation, composed of a male member 104 and a female receptacle 106, is provided. Male member 104 and female receptacle 106 are so arranged, relative to hook and loop fastener 108, that the hook and loop fastener can serve either as a back-up attachment means to the snap buckle or as the primary means by which front portion 100 and back portion 102 are attached.

While there have been described preferred embodiments of the present invention, it should be obvious to those skilled in the art that various modifications and changes can be made without departing from the true spirt and scope of the invention.

What is claimed:

1. A cervical collar comprising:
   a sternum brace having:
   (a) an extension adapted to extend to the sternum of a patient and including a flexible hinge portion, and
   (b) a padded movable footplate attached to said extension and adapted to rest against the sternum of the patient and permitted by said flexible hinge to move toward and away from the sternum of the patient:
   a back portion; and
   means for attaching said sternum brace and said back portion together.

2. A cervical collar comprising:
   a front portion;
   a back portion having:
   (a) a back support, and
   (b) an occipital support,
   (c) means for mounting said occipital support to said back support at an angle greater than forty-five degrees to said back support; and
   means for attaching said front portion and said back portion together.

3. A cervical collar according to claim 2 wherein said occipital support is mounted to said back support at substantially ninety degrees.

4. A cervical collar according to claim 2 wherein said occipital support is mounted to said back support for relative sliding movement between said occipital support and said back support.

5. A cervical collar comprising:
   a front portion having:
   (a) a sternum brace,
   (b) a jaw support, and
   (c) means for mounting said jaw support to said sternum brace so that said jaw support is disposed below the shoulder of a patient;
   a back portion; and means for attaching said front portion and said back portion together.

6. A cervical collar according to claim 5 wherein said jaw support is mounted to said sternum brace for relative sliding movement between said jaw support and said sternum brace.

7. A cervical collar according to claim 6 wherein said back portion includes:
   (a) a back support,
   (b) an occipital support, and
   (c) means for mounting said occipital support to said back support at an angle greater than forty-five degrees to said back support.

8. A cervical collar according to claim 7 wherein said occipital support is mounted to said back support for relative sliding movement between said occipital support and said back support.

9. A cervical collar comprising:
   a front portion;
   a back portion; and
   a snap buckle including:
      (a) a male member carried by said back portion, and
      (b) a female receptacle carried by said front portion for attaching said front portion to said back portion.

10. A cervical collar according to claim 9 further including a hook and loop fastener for attaching said front portion to said back portion.

11. A fastener unit for selective sliding movement between first and second workpieces, said fastening unit comprising:
   a first female member in the first workpiece and having:
      (a) first and second through-holes extending along first and second parallel axes, respectively, and
      (b) a through-passage extending between said first and said second through-holes,
   a second female member in the second workpiece and having a through-hole extending along an axis parallel to said first and said second axes of said first and said second through-holes in said first female member, and
   a male member movable:
      (a) axially through said first and said second through-holes in said first female member and said through-hole in said second female member, and
      (b) sidewise through said through-passage in said first female member, and having:
         (a) an enlarged head,
         (b) a first shank portion adjacent said enlarged head which:
            (1) limits axial movement of said male member in a first direction when said first shank portion abuts against said first female member, and
            (2) is sized relative to said through-passage in said first female member to prevent sidewise movement of said male member between said first and said second through-holes in said first female member when said male member is in a first axial position,
         (c) an enlarged tip which inibits axial movement of said male member in a second direction, opposite to the first direction, when said enlarged tip abuts against said second female member,
         (d) a second shank portion adjacent said first shank portion and sized relative to said through-passage in said first female member to permit sidewise movement of said male member between said first and said second through-holes in said first female member when said male member is in a second axial position, and
         (e) a third shank portion adjacent said enlarged tip in bearing contact with said second female member which inhibits axial movement of said male member in said second direction when said male member is in said first axial position and free of bearing contact with said second female member when said male member is in said second axial position.

12. A cervical collar comprising:
   a front portion having:
      (a) jaw support,
      (b) a sternum brace, and
      (c) means, including first and second spaced apart fastener units symmetrically disposed about a vertical center line of the cervical collar, for mounting said jaw support to said sternum brace for relative sliding movement between said jaw support and said sternum brace, each of said fastener units including:
         (1) a first female member in said sternum brace and having:
            (i) first and second through-holes extending along first and second parallel axes, respectively, and
            (ii) a through-passage extending between said first and said second through-holes,
         (2) a second female member in said jaw support and having a through-hole extending along an axis parallel to said first and said second axes of said first and said second through-holes in said first female member, and
         (3) a male member movable:
            (i) axially through said first and said second through-holes in said first female member and said through-hole in said second female member, and
            (ii) sidewise through said through-passage in said first female member,
         and having:
            (i) an enlarged head,
            (ii) a first shank portion adjacent said enlarged head which:
               limits axial movement of said male member in a first direction when said first shank portion abuts against said first female member, and
               is sized relative to said through-passage in said first female member to prevent sidewise movement of said male member between said first and said second through-holes in said first female member when said male member is in a first axial position,
            (iii) an enlarged tip which inhibits axial movement of said male member in a second direction, opposite to the first direction, when said enlarged tip abuts against said second female member,
            (iv) a second shank portion adjacent said first shank portion and sized relative to said through-passage in said first female member to permit sidewise movement of said male member between said first and said second through-holes in said first female member when said male member is in a second axial position, and
            (v) a third shank portion adjacent said enlarged tip in bearing contact with said second female member which inhibits axial movement of said male member in said second direction when said male member is in said first axial position and free of bearing contact with said second female member when said male member is in said second axial position;

a back portion; and means for attaching said front portion and said back portion together.

13. A cervical collar comprising:

a front portion;

a back portion having:
- (a) back support,
- (b) an occipital support, and
- (c) means, including first and second spaced apart fastener units symmetrically disposed about a vertical center line of the cervical collar, for mounting said occipital support to said back support for relative sliding movement between said occipital support and said back support; each of said fastener units including:
  - (1) a first female member in said occipital support and having:
    - (i) first and second through-holes extending along first and second parallel axes, respectively, and
    - (ii) a through-passage extending between said first and said second through-holes,
  - (2) a second female member in said back support and having a through-hole extending along an axis parallel to said first and said second axes of said first and said second through-holes in said first female member, and
  - (3) a male member movable:
    - (i) axally through said first and said second through-holes in said first female member and said through-hole in said second female member, and
    - (ii) sidewise through said through-passage in said first female member,
  - and having:
    - (i) an enlarged head,
    - (ii) a first shank portion adjacent said enlarged head which:
      - limits axial movement of said male member in a first direction when said first shank portion abuts against said first female member, and
      - is sized relative to said through-passage in said first female member to prevent sidewise movement of said male member between said first and said second through-holes in said first female member when said male member is in a first axial position,
    - (iii) an enlarged tip which inhibits axial movement of said male member in a second direction, opposite to the first diretion, when said enlarged tip abuts against said second female member,
    - (iv) a second shank portion adjacent said first shank portion and sized relative to said through-passage in said first female member to permit sidewise movement of said male member between said first and said second through-holes in said first female member when said male member is in a second axial position, and
    - (v) a third shank portion adjacent said enlarged tip in bearing contact with said second female member which inhibits axial movement of said male member in said second direction when said male member is in said first axial position and free of bearing contact with said second female member when said male member is in said second axial position; and means for attaching said front portion and said back portion together.

14. A cervical collar comprising:

a front portion having:
- (a) jaw support,
- (b) a sternum brace having:
  - (1) an extension adapted to extend to below the clavicle of a patient, and
  - (2) a padded movable footplate attached to said extension and adapted to rest against the body of the patient, and
- (c) means for mounting said jaw support to said sternum brace for relative sliding movement between said jaw support and said sternum brace;

a back portion; and means for attaching said front portion and said back portion together.

15. A cervical collar comprising:

a front portion having:
- (a) jaw support,
- (b) a sternum brace having:
  - (1) an extension adapted to extend to below the clavicle of a patient, and
  - (2) a padded movable footplate attached to said extension and adapted to rest against the body of the patient, and
- (c) means for mounting said jaw support to said sternum brace for relative sliding movement between said jaw support and said sternum brace;

a back portion having:
- (a) a back support,
- (b) an occipital support, and
- (c) means for mounting said occipital support to said back support for relative sliding movement between said occipital support and said back support; and means for attaching said front portion and said back portion together.

16. A cervical collar according to claim 14 wherein said mounting means include first and second spaced apart fastener units symmetrically disposed about a vertical center line of the cervical collar.

17. A cervical collar according to claim 15 wherein said mounting means include first and second spaced apart fastener units symmetrically disposed about a vertical center line of the cervical collar.

18. A cervical collar according to claim 15 wherein said extension includes a flexible hinge portion by which said padded movable footplate is permitted to pivot and move toward and away from the body of the patient.

19. A cervical collar comprising:

a sternum brace having:
- (a) an extension adapted to extend to below the clavicle of a patient and having a flexible hinge portion, and
- (b) a padded movable footplate attached to said extension and permitted by said flexible hinge portion to pivot and move (1) toward and rest against the body of a patient, and (2) away from the body of the patient;

a back portion; and means for attaching said sternum brace and said back portion together.

* * * * *

UNITED STATES PATENT AND TRADEMARK OFFICE
CERTIFICATE OF CORRECTION

PATENT NO.  : 6,254,560 B1
DATED       : July 3, 2001
INVENTOR(S) : Tweardy et al.

It is certified that error appears in the above-identified patent and that said Letters Patent is hereby corrected as shown below:

Column 2,
Line 44, please change "tree" to -- three --; and
Line 51, please change "ar." to -- an --.

Column 4,
Line 43, please change "through-hcle" to -- through-hole --.

Signed and Sealed this

Ninth Day of April, 2002

Attest:

Attesting Officer

JAMES E. ROGAN
Director of the United States Patent and Trademark Office